(12) United States Patent
Ballini (10) Patent No.: US 11,290,125 B2
(45) Date of Patent: Mar. 29, 2022

(54) MULTIPLEXED TWO-STEP NEURAL ADC

(71) Applicant: IMEC VZW, Leuven (BE)

(72) Inventor: Marco Ballini, Leuven (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 17/128,095

(22) Filed: Dec. 19, 2020

(65) Prior Publication Data

US 2021/0194495 A1   Jun. 24, 2021

(30) Foreign Application Priority Data

Dec. 20, 2019   (EP) .................................... 19218784

(51) Int. Cl.
*H03M 3/00* (2006.01)
*A61N 1/02* (2006.01)

(52) U.S. Cl.
CPC ............ *H03M 3/462* (2013.01); *A61N 1/025* (2013.01); *H03M 3/422* (2013.01); *H03M 3/47* (2013.01)

(58) Field of Classification Search
CPC .................................. H03M 3/00; H03M 1/14
See application file for complete search history.

(56) References Cited

U.S. PATENT DOCUMENTS

| | | | |
|---|---|---|---|
| 6,411,242 B1 | 6/2002 | Oprescu et al. | |
| 6,697,006 B1 * | 2/2004 | McCartney | ........... H03M 1/124 341/143 |
| 9,325,340 B2 | 4/2016 | Gonen et al. | |
| 9,455,737 B1 | 9/2016 | Rajaee et al. | |
| 9,660,662 B2 | 5/2017 | Venca et al. | |
| 10,270,460 B1 * | 4/2019 | Buffa | ........................ H03M 1/60 |
| 10,886,930 B1 * | 1/2021 | Buffa | .................. H03M 1/1245 |
| 2011/0304490 A1 * | 12/2011 | Janakiraman | .......... H03K 5/249 341/122 |
| 2017/0296080 A1 | 10/2017 | Yoon et al. | |
| 2018/0167079 A1 | 6/2018 | Ding et al. | |
| 2019/0253069 A1 | 8/2019 | Kim et al. | |

FOREIGN PATENT DOCUMENTS

| | | |
|---|---|---|
| KR | 101902972 B1 | 10/2018 |
| WO | WO-2012/177654 A2 | 12/2012 |

OTHER PUBLICATIONS

Markus et al., "Theory and Applications of Incremental ΔΣ Converters", IEEE Transactions on Circuits and Systems—I: Regular Papers, vol. 51, No. 4, pp. 678-690, Apr. 2004.

(Continued)

*Primary Examiner* — Lam T Mai
(74) *Attorney, Agent, or Firm* — Moser Taboada (57) ABSTRACT

An analog-to-digital converter, ADC, module is configured to operate in a coarse conversion ADC phase, and a fine conversion ADC phase comprising a delta modulation loop for tracking a signal, wherein the ADC module is configured to, at initiation of input of an analog signal, operate in the coarse conversion ADC phase for determining a coarse digital value; wherein the ADC module is configured to, when the coarse digital value is determined, operate in the fine conversion ADC phase, receive the coarse digital value as an initial approximation of the analog signal and track the analog signal during a finite duration.

16 Claims, 5 Drawing Sheets

(56) References Cited

OTHER PUBLICATIONS

Stensgaard et al., "Noise-Power Optimization of Incremental Data Converters", IEEE Transactions on Circuits and Systems I:Regular Papers, vol. 55, No. 5, pp. 1289-1296, Jun. 2008.

Temes et al., "Incremental Data Converters", Proceedings of 19th International Symposium on Mathematical Theory of Networks and Systems, pp. 715-721, Jul. 5-9, 2010.

Chae et al., "A 6.3 µW 20 bit Incremental Zoom-ADC with 6 ppm INL and 1 µV Offset", IEEE Journal of Solid-State Circuits, vol. 48, No. 12, pp. 3019-3027, Dec. 2013.

Yaul et al., "A 10 bit SAR ADC With Data-Dependent Energy Reduction Using LSB-First Successive Approximation", IEEE Journal of Solid-State Circuits, vol. 49, No. 12, pp. 2825-2834, Dec. 2014.

Park et al., "Toward 1024 channel parallel neural recording: Modular $\Delta$-$\Delta$ $\Sigma$ analog front-end architecture with 4.84fJ/C-s mm2 energy-area product", IEEE Symposium on VLSI Circuits, pp. C112-C113, 2015.

Raducanu et al., "Time-multiplexed active neural probe with 678 parallel recording sites", 2016 46th European Solid-State Device Research Conference, pp. 385-388, Sep. 2016.

Smith et al., "A Scalable, Highly-Multiplexed Delta-Encoded Digital Feedback ECoG Recording Amplifier with Common and Differential-Mode Artifact Suppression", 2017 Symposium on VLSI Circuits, pp. C172-C173, 2017.

Mora Lopez et al., "A Neural Probe With Up to 966 Electrodes and Up to 384 Configurable Channels in 0.13 µm SOI CMOS", IEEE Transactions on Biomedical Circuits and Systems, vol. 11, No. 3, pp. 510-522, Jun. 2017.

Gönen et al., "A Dynamic Zoom ADC With 109-dB DR for Audio Applications", IEEE Journal of Solid-State Circuits, vol. 52, No. 6, pp. 1542-1550, Jun. 2017.

Kassiri et al., "Rail-to-Rail-Input Dual-Radio 64-Channel Closed-Loop Neurostimulator", IEEE Journal of Solid-State Circuits, vol. 52, No. 11, pp. 2793-2810, Nov. 2017.

Huang et al., "A 0.01-mm$^2$ Mostly Digital Capacitor-Less AFE for Distributed Autonomous Neural Sensor Nodes", IEEE Solid-State Circuits Letters, vol. 1, No. 7, pp. 162-165, 2018.

Shui et al., "A 70.8 dB 0.0045 mm$^2$ Low-power Continuous-Time Incremental Delta-Sigma Modulator for Multi-Site Neural Recording Interfaces", IEEE International Symposium on Circuits and Systems, pp. 1-4, 2018.

Park et al: "Modular 128-Channel $\Delta$-$\Delta$ $\Sigma$ Analog Front-End Architecture Using Spectrum Equalization Scheme for 1024-Channel 3-D Neural Recording Microsystems", IEEE Journal of Solid-State Circuits, vol. 53, No. 2, pp. 501-514, Feb. 2018.

Hsieh et al., "A 0.4V 13b 270kS/s SAR-ISDM ADC with an Opamp-Less Time-Domain Integrator", 2018 IEEE International Solid-State Circuits Conference, vol. 61, pp. 240-242, Feb. 13, 2018.

De Dorigo et al., "A Fully Immersible Deep-Brain Neural Probe With Modular Architecture and a Delta-Sigma ADC Integrated Under Each Electrode for Parallel Readout of 144 Recording Sites", 2018 IEEE International Solid-State Circuits Conference, pp. 462-464, Feb. 14, 2018.

Dimitriadis et al., "Why not record from every channel with a CMOS scanning probe?", bioRxiv, p. 275818, Mar. 3, 2018.

Almarashli et al., "A Nyquist Rate SAR ADC Employing Incremental Sigma Delta DAC Achieving Peak SFDR=107 dB at 80 kS/s", IEEE Journal of Solid-State Circuits, vol. 53, No. 5, pp. 1493-1507, May 2018.

Kim et al., "Sub-µV$_{rms}$-Noise Sub-µW/Channel ADC-Direct Neural Recording With 200-mV/ms Transient Recovery Through Predictive Digital Autoranging", IEEE Journal of Solid-State Circuits, vol. 53, No. 11, pp. 3101-3110, Oct. 2018.

De Dorigo et al., "Fully Immersible Subcortical Neural Probes With Modular Architecture and a Delta-Sigma ADC Integrated Under Each Electrode for Parallel Readout of 144 Recording Sites", IEEE Journal of Solid-State Circuits, vol. 53, No. 11, pp. 3111-3125, Nov. 2018.

Ivanisevic et al., "A 14-ENOB Delta-Sigma Based Readout Architecture for ECoG Recording Systems", IEEE Transactions on Circuits and Systems I:Regular Papers, vol. 65, No. 12, pp. 4051-4061, Dec. 2018.

Extended European Search Report for Application No. EP 19218784.7, dated Jun. 16, 2020.

* cited by examiner

MULTIPLEXED TWO-STEP NEURAL ADC

CROSS-REFERENCE TO RELATED APPLICATION

The present application is based on priority claimed on European Patent Application No. 19218784.7, filed on Dec. 20, 2019, the contents of which are incorporated herein by reference.

TECHNICAL FIELD

The present inventive concept relates to analog-to-digital conversion of electrical signals. In particular, the present inventive concept relates to analog-to-digital conversion of multiplexed analog signals.

BACKGROUND

In various sensor systems, a large array of sensors is used, e.g. in order to provide high spatial resolution of sensing. For instance, an array of electrodes may be used in a neural probe for detecting neural signals from brain tissue. In such case, it may be important that the electrode resolution is high in order to enable detecting signals from a large number of neurons.

In order to allow high resolution sensing of electrical signals, it may be beneficial that processing of several electrical signals is shared within a single circuitry, such as an analog-to-digital converter (ADC) circuitry. The ADC circuitry may thus receive a time division multiplexed sequence of a plurality of analog signals so as to support plural sensors within an array. This implies that the ADC circuitry/circuitries may consume a relatively small area and that a sensor pitch may be relatively small. Also, using a multiplexed sequence may facilitate using relatively few wires for transmitting the electrical signals from the array of sensors to the ADC circuitry/circuitries, which may allow use of a small overall size of a carrier carrying the array of sensors. This may be particularly beneficial for a neural probe so as to allow limiting an impact of tissue damage by inserting a neural probe into brain tissue.

The analog signals within the plurality of multiplexed analog signals may have very different DC offsets. For instance, when recording electrical signals in a brain, a large and random DC offset caused by an electrode-brain interface may be over-imposed to a minute electric signals recorded by the electrode.

A large differing DC offset of the multiplexed signals may be handled by using an ADC circuitry having a large dynamic range. Delta modulation may be used in the ADC circuitry in order to have a large dynamic range, but delta modulation may on the other hand require a long processing time before a modulator reaches a level of an input voltage of a new sub-sequence within the multiplexed signal.

In Hsieh et al, "A 0.4V 13b 270 kS/s SAR-ISDM ADC with an Opamp-Less Time-Domain Integrator", 2018 IEEE International Solid-State Circuits Conference, Digest of technical papers, pages 240-242, Feb. 13, 2018, there is disclosed an architecture of a 13b ADC consisting of two sub-ADCs, an on-chip $V_{cm}$ reference generator, and a global control unit. For each sub-ADC, a 9b digital-to-analog converter (DAC) with unit capacitance of 5.4 fF and an incremental sigma-delta modulator (ISDM) with time-domain integrator are implemented for 10b coarse successive approximation register (SAR) conversion and 4b fine conversion, respectively. Thus, the coarse conversion is used for most significant bit conversion and the fine conversion is used for least significant bit conversion.

There may still be a need of improving analog-to-digital conversion of analog signals, in particular for conversion of a time division multiplexed signal.

SUMMARY

It is an object of the present inventive concept to provide an ADC circuitry for analog-to-digital conversion of analog signals that may quickly settle on a digital value. It is a particular object of the present inventive concept to facilitate following analog values of a sub-sequence within a multiplexed analog signal for analog-to-digital conversion of the sub-sequence.

These and other objects of the invention are at least partly met by the invention as defined in the independent claims. Preferred embodiments are set out in the dependent claims.

According to an aspect of the present inventive concept there is provided an analog-to-digital converter (ADC) module, wherein the ADC module is configured to operate in a coarse conversion ADC phase, and a fine conversion ADC phase comprising a delta modulation loop for tracking a signal, wherein the ADC module is configured to, at initiation of input of an analog signal, operate in the coarse conversion ADC phase for determining a coarse digital value of the analog signal; wherein the ADC module is configured to, when the coarse digital value is determined, operate in the fine conversion ADC phase, wherein the ADC module operating in the fine conversion ADC phase is configured to receive the coarse digital value as an initial approximation of the analog signal and is configured to track the analog signal during a finite duration.

Thanks to the present inventive concept, the ADC module is configured to operate in a coarse conversion ADC phase and a fine conversion ADC phase. The fine conversion ADC phase using a delta modulation loop may support analog-to-digital conversion with a large dynamic range. The coarse conversion ADC phase may allow quickly determining an initial approximation for the fine conversion ADC phase so as to support quickly settling on a digital value of the analog signal. This may be particularly beneficial for analog-to-digital conversion of a multiplexed sequence comprising sub-sequences of different analog signals, if there are large variations in DC offset of different analog signals in the multiplexed sequence. After settling, the fine conversion ADC phase may further track the analog signal within the sub-sequence so as to allow quickly following the analog signal.

It should be realized that the ADC module may be beneficially used also for conversion of a single analog signal. The coarse conversion ADC phase may allow quickly settling on a digital value and the fine conversion ADC phase allows tracking of the analog signal. The finite duration may correspond to the Nyquist rate.

However, the ADC module may alternatively be configured for tracking the analog signal during a longer finite duration. In such case, if there is a very fast change in the input analog signal, such as a large artefact which may bring an electrode voltage input to the ADC module to deviate temporarily and significantly from its normal DC voltage offset, the coarse conversion ADC phase may be re-initiated before fine conversion ADC phase continues based on a new coarse digital value as an initial approximation. The tracking of a single analog signal may, even if no fast changes in the signal are detected, be performed during a finite duration, after which the ADC module may again operate in the coarse conversion ADC phase before tracking the analog signal in the fine conversion ADC phase. For instance, the finite duration may be a minute or ten seconds.

The fine conversion ADC phase may track the analog signal regardless of a value of the initial approximation from the coarse conversion phase so that the coarse conversion ADC phase does not set limits on a range of possible digital values that may later be determined by the fine conversion ADC phase. In particular, the fine conversion ADC phase does not digitize a residue of the coarse conversion ADC phase.

The tracking of the analog signal provides an oversampling of the analog signal enabling output of a digital signal that follows the analog signal.

The delta modulation loop is configured to determine the difference between a current value of the signal and a previous value of the signal, whereby the delta modulation loop may be used for tracking changes of the analog signal. The delta modulation loop may comprise a quantizer having a single-bit comparator, whereby the tracking of the analog signal may be configured to change at most one bit at a time. However, the delta modulation loop could alternatively use a multi-bit comparator, which may be more complex, but may more quickly handle larger variations in the analog signal. The delta modulation loop may provide oversampled data at a high rate. This oversampled data may then be averaged and down-sampled for providing high resolution digital values, but at a lower rate.

It should be realized that the ADC module may comprise a first circuitry portion which is dedicated to performing the coarse conversion ADC phase, and a second circuitry portion which is dedicated to performing the fine conversion ADC phase. In such case, the ADC module may, at initiation of input of an analog signal, be configured to provide the analog signal to the first circuitry portion for performing the coarse conversion ADC phase. When the coarse digital value is determined, the ADC module may be configured to provide the analog signal to the second circuitry portion for performing the fine conversion ADC phase. However, according to an alternative, the ADC module may comprise a circuitry portion which may be set into different configurations for performing both the coarse conversion ADC phase and the fine conversion ADC phase. In such case, the ADC module may re-use components for use in both the coarse conversion ADC phase and the fine conversion ADC phase, which may allow the ADC module to be compact.

According to an embodiment, the fine conversion ADC phase is configured to receive the coarse digital value as an initial approximation of the analog signal in an integrator of the delta modulation loop. This is suitable for providing the initial approximation to the fine conversion ADC phase.

According to an embodiment, the ADC module in the fine conversion ADC phase provides an incremental ADC.

An incremental ADC may be formed as a delta-delta-sigma ADC comprising an inner delta-sigma modulator, wherein integrators of the inner delta-sigma modulator are reset periodically. This implies that the incremental ADC may be well suited for analog-to-digital conversion of time-multiplexed signals. Also, in the ADC circuitry of the present inventive concept, a comparator used for the coarse conversion ADC phase may be re-used in the fine conversion ADC phase.

However, it should be realized that the incremental ADC may alternatively use a quantizer based on one or more ring oscillators, wherein the oscillators are periodically reset, or other type of quantizer.

According to an embodiment, the ADC module in the fine conversion ADC phase provides a delta-delta-sigma modulator ADC comprising an inner delta-sigma modulator with an outer delta modulator.

The delta-delta-sigma ADC provides a digital conversion of the analog signal using the coarse conversion ADC phase as an initial estimation of the analog signal, functioning as a tracking ADC. The delta modulator is called an "outer" delta modulator since feedback from the delta modulator is subtracted from the analog signal before the analog signal is further provided to the inner delta-sigma modulator.

According to an embodiment, the outer delta modulator comprises a digital integrator followed by a digital-to-analog converter (DAC).

The DAC may be a multi-bit DAC. This may be particularly advantageous, because it allows re-using the DAC for providing an analog representation of a coarse value during successive approximation in the coarse conversion ADC phase and for providing analog delta feedback in the fine conversion ADC phase.

According to an alternative, the outer delta modulator may comprise a single-bit DAC followed by an analog integrator for providing the delta feedback.

According to an embodiment, the ADC module is configured to operate in the coarse conversion ADC phase using successive approximation.

The successive approximation may successively determine bit values to represent the analog signal by a coarse digital value, wherein the successive approximation may start by determining the bit value of a most significant bit successively proceeding to less significant bits. The successive approximation may be implemented as a successive approximation register (SAR) ADC. However, in contrast to typical SAR ADCs, the successive approximation of the coarse conversion ADC phase need not necessarily start without any assumption of the analog value (initiated e.g. to zero). Rather, the successive approximation of the coarse conversion ADC phase could use a (stored) value of the analog signal in a previous sub-sequence of the same signal as an initial approximation of the coarse digital value to be determined by the successive approximation.

According to an embodiment, the inner delta-sigma modulator comprises at least one integrator, and wherein the ADC module is configured to, when the coarse digital value is determined, reset the at least one integrator of the inner delta-sigma modulator.

However, it should be realized that the inner delta-sigma modulator need not necessarily comprise an integrator but may alternatively comprise another type of filter. Also, it should be realized that the inner delta-sigma modulator may comprise one or more integrators (or other types of filters) depending of an order of the delta-sigma modulator.

As the inner delta-sigma modulator may provide an incremental ADC, the integrators are periodically reset. The resetting of the at least one integrator may be performed at start of the fine conversion ADC phase. However, since the at least one integrator is not used during the coarse conversion ADC phase, the at least one integrator may actually be reset e.g. during the coarse conversion ADC phase instead.

According to an embodiment, the ADC module is connected to a decimation filter for providing output from the ADC module operating in the fine conversion ADC phase to the decimation filter for down-sampling of output from the fine conversion ADC phase.

The decimation filter may provide down-sampling to provide an average of oversampled data from the fine conversion ADC phase, providing a higher resolution value of the analog signal at a lower rate. The decimation filter may down-sample the output from the fine conversion ADC phase to the Nyquist rate.

The decimation filter may be connected to receive output from the ADC module operating in the fine conversion ADC phase. The decimation filter need not be connected to receive output from the coarse conversion ADC phase but may rather only be connected to receive output from the fine conversion ADC phase. The coarse digital value provided by the coarse conversion ADC phase on the other hand need only be provided as an initial approximation to the fine conversion ADC phase and need therefore not be connected to the decimation filter.

According to an embodiment, the decimation filter is configured to provide different weights to different individual oversampled values.

The individual oversampled values comprise at least a first sample value and a second sample value which is provided later in time than the first sample value. In one embodiment, the second sample value is provided with a higher weight. However, non-monotonic weighting may also be used.

The use of different weights to different oversampled values may reduce effects of non-linearity of a feedback DAC that may be used in the coarse conversion ADC phase. The non-linearity of a feedback DAC in fine conversion ADC phase may be reduced using a mismatch-shaping algorithm, which may not be possible to use in the coarse conversion ADC phase, since the coarse conversion ADC phase may not provide oversampling of data. Thus, by giving a higher weight to last sample values in the fine conversion ADC phase compared to initial sample values, a contribution of the initial sample values is reduced and an error in initial values caused by the non-linearity of the coarse conversion ADC phase may be diminished or reduced.

According to an embodiment, the ADC module in the fine conversion ADC phase provides an element selection logic for dynamic-element-matching of the multi-bit DAC used in the outer delta-modulator.

An effect of any non-idealities in the ADC module, e.g. non-linearity of a DAC in the delta modulator, may be reduced by the element selection logic for dynamic-element-matching (DEM). For instance, mismatch-shaping or transition-error shaping techniques may be applied. According to an embodiment, Dynamic Weighted Averaging (DWA) may be applied during the fine conversion ADC phase.

It should be realized that the inner delta-sigma modulator could also in some embodiments use a DAC. In such case, DEM may also be used in the inner delta-sigma modulator.

According to an embodiment, the successive approximation of the coarse conversion ADC phase is configured to be executed in a number of cycles corresponding to a number of bits supported by a multi-bit digital-to-analog converter, DAC.

The coarse conversion ADC phase may quickly determine a coarse digital value of the analog signal. In each cycle of the successive approximation, a bit for representing the analog signal may be tested and the value (zero or one) of the bit to be used may be determined by comparison of a test value to the analog signal. Thus, the successive approximation may iteratively determine bit values starting at a most significant bit and proceeding towards successively less significant bits.

However, it should be understood that the coarse conversion ADC phase need not be executed in exactly a number of cycles corresponding to the number of bits. Rather, the successive approximation could for instance use 13 cycles for determining 12 bit values.

According to an embodiment, the ADC module is configured to be controlled to selectively activate the coarse conversion ADC phase or the fine conversion ADC phase.

The ADC module may be configured to use at least partly common components for coarse conversion ADC phase and fine conversion ADC phase. The ADC module may thus be controlled to activate components corresponding to the ADC phase to be performed, such that functionality of the ADC module is dynamically changed between providing the coarse conversion ADC phase or the fine conversion ADC phase.

According to an embodiment, the ADC module is configured to re-use at least one component, such as a multi-bit DAC and/or a single-bit comparator, when operating in the coarse conversion ADC phase and the fine conversion ADC phase.

Since the coarse conversion ADC phase and the fine conversion ADC phase may be performed sequentially in time, re-use of components for both phases is facilitated. Thanks to the re-use of components, the ADC module may be compact.

According to a second aspect, there is provided an ADC circuitry, comprising: a multiplexer input configured to receive a plurality of analog signals and configured to output a time division multiplexed sequence of the plurality of analog signals, wherein each of the plurality of analog signals forms at least one sub-sequence within the sequence, and the ADC module; wherein the ADC module is configured to, at initiation of a sub-sequence of an analog signal within the sequence of the plurality of analog signals, operate in the coarse conversion ADC phase, and wherein the ADC module operating in the fine conversion ADC phase is configured to track the analog signal during the sub-sequence.

Effects and features of this second aspect are largely analogous to those described above in connection with the first aspect. Embodiments mentioned in relation to the first aspect are largely compatible with the second aspect.

Thus, the ADC module may be implemented in an ADC circuitry for analog-to-digital conversion of a plurality of multiplexed signals. The ADC module may be particularly useful in analog-to-digital conversion of a multiplexed sequence, since it may handle large variations in DC offset of the different analog signals in the multiplexed sequence.

It should be realized that the ADC module being configured to, at initiation of a sub-sequence of an analog signal within the sequence of the plurality of analog signals, operate in the coarse conversion ADC phase does not necessarily imply that the ADC module will operate in the coarse conversion ADC phase as defined for all sub-sequences of the analog signal. For instance, the ADC module may operate as a SAR ADC in the coarse conversion ADC phase for the first sub-sequence of the analog signal within the sequence, whereas the ADC module for other sub-sequences than the first sub-sequence may utilize successive approximation using a value of the analog signal of the previous sub-sequence of the same signal as an initial approximation of the coarse digital value. Also, it may be envisaged that the ADC module at initiation of a sub-sequence makes an initial comparison of the analog signal to a stored value of a previous sub-sequence of the same signal and, if a difference of the analog signal and the stored value is below a threshold, the ADC module may proceed directly to the fine conversion ADC phase using the stored value without need of performing the coarse conversion ADC phase for the sub-sequence.

Each sub-sequence within the time division multiplexed sequence of the plurality of analog signals may have an equal duration. However, this is not strictly necessary, and it should be realized that varying durations may also be used.

The ADC module may be configured to operate in the coarse conversion ADC phase receiving output from the multiplexer and to operate in the fine conversion ADC phase receiving output from the multiplexer. Hence, the multiplexer may be arranged in front of the ADC module to provide output to the ADC module.

However, it should be realized that the multiplexer need not necessarily be arranged in front of the ADC module. Rather, a part of the ADC module may be arranged in front of the multiplexer. For instance, a transconductor stage may be provided in front of the multiplexer. Then, multiplexing would be done in current domain. This may be beneficial in reducing input impedances of sensors connected to the ADC circuitry.

It should be realized that although mainly discussed herein in relation to detecting electrical signals in neural probes, the analog-to-digital conversion for time division multiplexed sequences of analog signals may be performed in other applications as well.

According to an embodiment, each of the plurality of analog signals forms at least a first sub-sequence and a second sub-sequence within the sequence, wherein the ADC circuitry further comprises a memory for storing an end value determined by tracking the analog signal during the first sub-sequence, and wherein the ADC module is configured to, at initiation of the second sub-sequence of the analog signal, operate in the coarse conversion ADC phase receiving output from the multiplexer for determining a coarse digital value of the analog signal and receiving the end value from the memory as an initial approximation for determining the coarse digital value.

By storing the end value from tracking the analog signal, the ADC circuitry may provide an initial guess of a value of the analog signal when a subsequent sub-sequence of the analog signal is initiated. This initial guess may be closer to the analog signal than a default guess (such as setting an initial approximation to zero) and may hence allow more quickly determining the coarse digital value.

According to a third aspect, there is provided a sensor unit comprising: a set of sensors configured to record electrical signals; and the ADC circuitry according to the second aspect, wherein the ADC circuitry is connected to at least a subset of the set of sensors for receiving the plurality of analog signals.

Effects and features of this third aspect are largely analogous to those described above in connection with the second and third aspects. Embodiments mentioned in relation to the first and second aspects are largely compatible with the third aspect.

The sensors may be any type of sensor that is configured to generate and record an electrical signal. The sensor may be configured to directly sense an electrical signal and may hence e.g. be provided in the form of an electrode. However, the sensor may alternatively be e.g. a transducer which is able to convert a sensed property to an electrical signal.

The sensor unit is particularly useful in applications where the set of sensors may have significant DC offset variations, as the coarse conversion ADC phase allows the ADC circuitry to quickly settle on a new analog signal value which may significantly differ from a previous analog signal value in the sequence.

The sensor unit may comprise a plurality of ADC circuitries, wherein each ADC circuitry is configured to perform analog-to-digital conversion for signals from a unique subset of the set of sensors. Thus, the number of ADC circuitries may be less than the number of sensors in the set of sensors. Each ADC circuitry may for instance support four sensors, 16 sensors or even 64 sensors, or any number of sensors in a range of 4-64.

According to a fourth aspect, there is provided a neural probe comprising: a carrier adapted for being inserted into neural tissue of a brain; the sensor unit according to the third aspect, wherein the set of sensors is arranged on the carrier for recording electrical signals from sensing in the brain.

Effects and features of this fourth aspect are largely analogous to those described above in connection with the first, second, and third aspects. Embodiments mentioned in relation to the first, second, and third aspects are largely compatible with the fourth aspect.

The ADC circuitry of the second aspect is particularly useful in a neural probe. As the ADC circuitry may support a plurality of sensors (electrodes) in the neural probe, the ADC circuitry/circuitries may consume a relatively small area. Thus, the ADC circuitry may be arranged on the carrier which is arranged to be inserted into the brain while the size of the carrier may be relatively small so as to limit an impact of tissue damage by the insertion of the neural probe into brain tissue. In this case fewer number of wires than electrodes are needed to transmit the digitized data. This can increase the number of electrodes that can be integrated on a portion of the carrier inserted into neural tissue. The number of electrodes is typically limited by the number of wires that can be routed within the small cross-section of the inserted portion. Furthermore, the digital output from several ADCs can also be combined into a reduced number of wires than the number of ADCs. However, the ADC module need not be arranged on the portion of the carrier that is inserted into the neural tissue. Rather, the ADC module may alternatively be arranged on a portion of the carrier (or on another unit of the neural probe) which is not inserted into the neural tissue. Still, thanks to the ADC module supporting a plurality of electrodes, a number of wires needed for transmitting signals from the electrodes to the ADC module may be reduced by having a multiplexer arranged on the portion of the carrier that is inserted. This may also limit a size of the portion of the carrier being inserted into the neural tissue.

Further, the DC offset of electrodes may typically vary significantly between different electrodes due to large and random DC offsets caused by the electrode-brain interface. Therefore, the ADC circuitry according to the first aspect, which is configured to handle large variations in DC offset in a time-multiplexed sequence, is particularly useful with the neural probe.

According to a fifth aspect, there is provided a microelectrode array, comprising: a carrier providing a surface for receiving a sample of biological matter; and the sensor unit according to the third aspect, wherein the set of sensors is arranged on the carrier for recording electrical signals in the sample of biological matter.

Effects and features of this fifth aspect are largely analogous to those described above in connection with the first, second, third, and fourth aspects. Embodiments mentioned in relation to the first, second, third, and fourth aspects are largely compatible with the fifth aspect.

The micro-electrode array may comprise a large number of sensors (electrodes). Thanks to the use of the ADC circuitry that may support a plurality of sensors, while enabling handling of large variations in DC offset, an area of circuitry needed for analog-to-digital conversion of recorded signals may be limited. This implies that the ADC circuitry may be arranged below the set of sensors and thereby the need of routing analog signals to a periphery of the micro-electrode array may be avoided. As in the fourth aspect, this can also enable the integration of a larger number or a higher density of electrodes, or a larger number of electrodes that can be simultaneously recorded, since the number of wires required for each subset of the electrodes can be reduced.

The "sample of biological matter" may include any type of matter of a living organism or originating from a once-living organism. Thus, the sample of biological matter may be laboratory grown cells, which may in fact be grown on the surface of the carrier, a sample of cells from a living organism, or a sample of tissue from a living organism, such as a brain slice.

According to an embodiment of the third aspect or the fourth aspect, the ADC circuitry is arranged on the carrier.

This implies that the ADC circuitry may for instance be arranged below sensors on the carrier. The arrangement of the sensor unit on the carrier may thus be provided in a very compact manner. The set of sensors and the ADC circuitry may thus for instance be integrated on a common substrate, such as a common silicon substrate.

According to a sixth aspect, there is provided a method for analog-to-digital conversion, said method comprising: receiving an analog signal, at initiation of the analog signal, performing a coarse analog-to-digital conversion for determining a coarse digital value of the analog signal; performing a fine analog-to-digital conversion using the coarse digital value as an initial approximation of the analog signal, wherein the fine analog-to-digital conversion uses a delta modulation loop for tracking the analog signal during a finite duration.

Effects and features of this sixth aspect are largely analogous to those described above in connection with the first, second, third, fourth, and fifth aspects. Embodiments mentioned in relation to the first, second, third, fourth, and fifth aspects are largely compatible with the sixth aspect.

The coarse analog-to-digital conversion may allow quickly determining an initial approximation for the fine analog-to-digital conversion so as to support quickly settling on a digital value for the analog signal. This is particularly beneficial if there occur large temporary variations in DC offset of the analog signal such that a coarse approximation may be performed when a large change in DC offset occurs. After settling, the fine analog-to-digital conversion may further track the analog signal so as to allow quickly following the analog signal. The fine analog-to-digital conversion using a delta modulation loop may also support analog-to-digital conversion with a large dynamic range.

According to an embodiment, the method comprises receiving a plurality of analog signals, wherein each of the plurality of analog signals forms at least one sub-sequence within a time division multiplexed sequence of the plurality of analog signals; at initiation of a sub-sequence of an analog signal within the sequence of the plurality of analog signals, performing the coarse analog-to-digital conversion, and performing the fine analog-to-digital conversion to track the analog signal during the sub-sequence.

This is particularly beneficial if there are large variations in DC offset of different analog signals in the multiplexed sequence.

According to an embodiment, the coarse analog-to-digital conversion is performed using successive approximation.

This may be a fast way of performing coarse analog-to-digital conversion.

According to an embodiment, the method further comprises outputting a sequence of analog-to-digital converted values from the fine analog-to-digital conversion to a decimation filter, and outputting a digital representation of the sub-sequence of the analog signal from the decimation filter.

The decimation filter may provide down-sampling of data to provide an average of oversampled data from the fine analog-to-digital conversion, providing a higher resolution value of the analog signal at a lower rate. The decimation filter may down-sample the output from the fine analog-to-digital conversion to the Nyquist rate.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Delta-sigma modulation may be used for analog-to-digital conversion of analog signals. In delta-sigma modulation, quantization error noise in a frequency band of interest is reduced by oversampling. To achieve low input-referred quantization noise, a large oversampling ratio (OSR) is used.

However, a too large oversampling ratio (e.g. >1000) corresponds to very large clock rate, which may incur large power consumption of a clock-distribution network. In particular, power consumption may be large when such high-frequency signals need to be carried in a long path, such as when clock signals are to be provided along a shank inserted into neural tissue of the brain (i.e. transmitting signals over several millimeters).

In the present inventive concept, delta modulation is used, which may provide an enhanced dynamic range of the delta-sigma modulator. Thus, the delta modulation may be provided around the delta-sigma modulator so as to form a delta-delta sigma modulator. The delta-delta sigma modulator may use a single-bit low-area quantizer, such as a comparator.

According to the present inventive concept, an analog-to-digital converter (ADC) circuitry may be used, wherein time division multiplexed sequence of a plurality of analog signals, each forming at least one sub-sequence within the sequence, are converted. Thanks to handling multiplexed signals, there is provided a reduction of circuitry area per sensor supported by the ADC circuitry. Thus, a single ADC circuitry may be associated with a plurality of sensors, wherein each sensor is configured to record an electrical signal, e.g. from neurons in neural tissue.

Although described below in relation to a multiplexed sequence, it should be realized that the analog-to-digital conversion may alternatively be applied to a single analog signal.

The delta modulation of the ADC circuitry may be configured to only increment one unit per sample. Therefore, at initiation of a sub-sequence of an analog signal, e.g. when switching from an analog signal of one sensor to an analog signal of another sensor, a large difference in a level of the electric signal (which may typically occur when sensing electrical signals in neural tissue, as different DC offsets of different sensors (electrodes) may be caused by the electrode-brain interface) can require many cycles of the delta modulator to reach the new signal level of the sub-sequence, before proper signal conversion can start. If the difference is large, modulator saturation can even occur, which can then require even longer time for settling.

Figure 1:
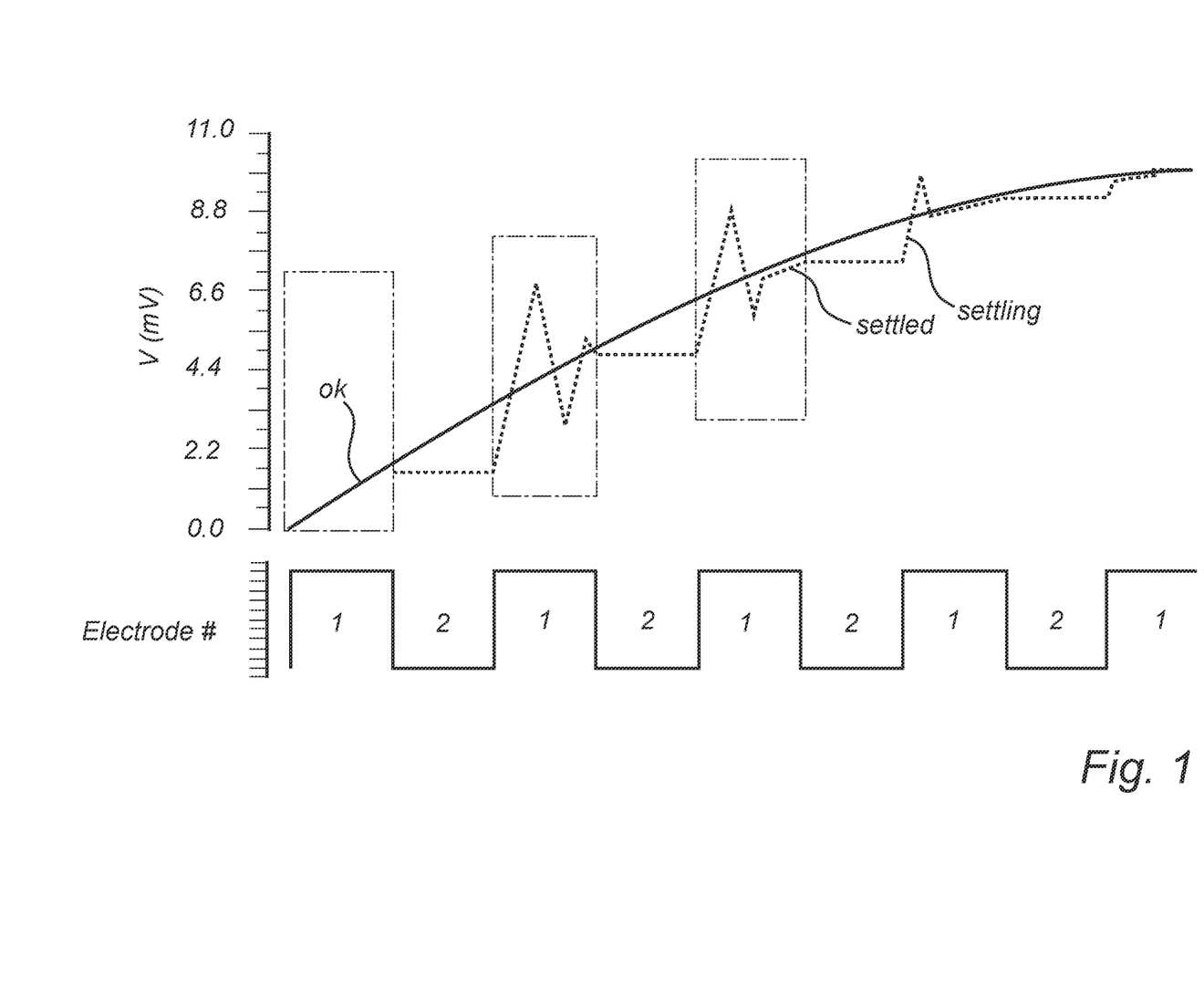
FIG. 1 is a schematic chart illustrating analog-to-digital conversion of an analog signal in a multiplexed sequence.

Referring now to FIG. 1, analog-to-digital conversion of a first analog signal (solid line), which is multiplexed with a second analog signal is illustrated. It should be realized that the use of only two channels (analog signals) is merely for illustration purposes, and that many more channels may be multiplexed.

A tentative solution to the problem of handling varying levels of the analog signals might be to simply hold in memory the offset of each analog signal (e.g. allocating one integrator/memory per channel) and using it when the corresponding analog signal is selected. A result of such use of a stored offset in analog-to-digital conversion is represented in FIG. 1, where output from an ADC circuitry for analog-to-digital conversion of the first analog signal is shown (dashed line).

Nonetheless, this tentative solution may not be effective, if the first analog signal undergoes large variations between subsequent sub-sequences of the first analog signal, as can be observed in FIG. 1. As shown in FIG. 1, in a new sub-sequence of the first analog signal, the modulator needs to quickly reach the new value present at an input of the ADC circuitry. However, this may not be happening quickly enough if a step from a previous value (of the previous sub-sequence of the first analog signal) is large. If the step is too large, saturation of the delta modulation can also occur resulting in several up-and-down phases before the output of the ADC circuitry settles and closely follows the input. This effect reduces the number of cycles available for fine conversion, thus degrading the available resolution.

Figure 2:
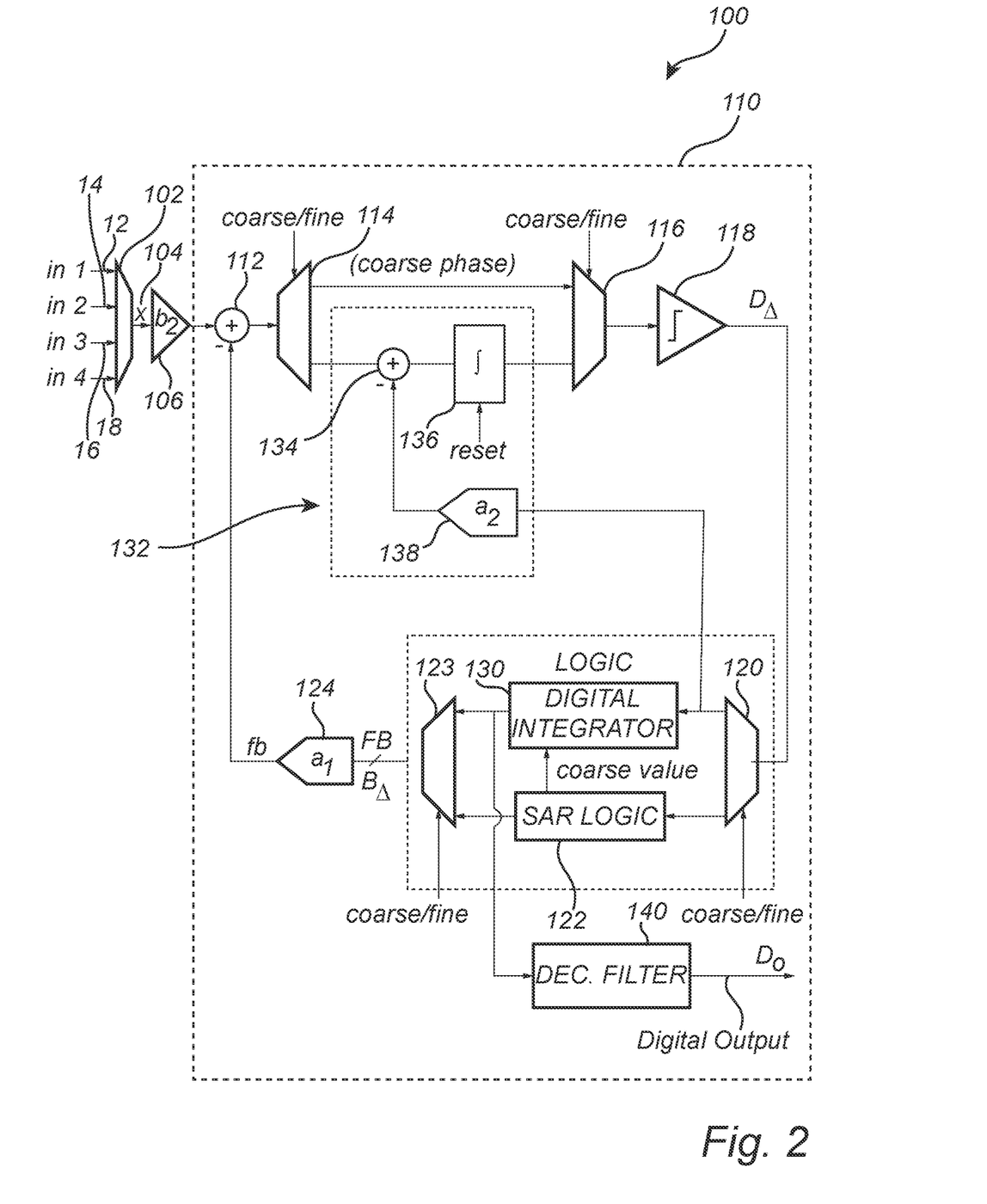
FIG. 2 is a schematic view of an analog-to-digital converter circuitry according to an embodiment.

Referring now to FIG. 2, an ADC circuitry 100 according to an embodiment will be discussed.

As illustrated in FIG. 2, a multiplexer 102 may have a multiplexer input, which may be connected to receive analog signals 12, 14, 16, 18 from a plurality of sensors. The sensors may for instance be electrodes that are configured to record electrical signals in neurons of neural tissue.

The multiplexer 102 may be configured to generate a time division multiplexed sequence 104 of the plurality of analog signals 12, 14, 16, 18 received by the multiplexer 102. Each of the plurality of analog signals 12, 14, 16, 18 may thus form a plurality of sub-sequences within the sequence, wherein the sub-sequences from different analog signals 12, 14, 16, 18 are interleaved in the multiplexed sequence 104.

The ADC circuitry 100 may comprise a transconductor stage 106 for converting the multiplexed sequence 104 to a current before performing analog-to-digital conversion. The transconductor stage 106 may alternatively be arranged in front of the multiplexer 102.

As illustrated in FIG. 2, the ADC circuitry 100 may further comprise an ADC module 110, which may be dynamically configured to perform coarse analog-to-digital conversion in a coarse conversion ADC phase or fine analog-to-digital conversion in a fine conversion ADC phase. Hence, one or more components of the ADC module 110 may be re-used in the coarse conversion ADC phase and the fine conversion ADC phase.

However, it should be realized that alternatively the ADC module 110 may comprise a first and a second circuitry portion, the first circuitry portion being separate from the second circuitry portion. The first circuitry portion may be configured to operate in a coarse conversion ADC phase, whereas the second circuitry portion may be configured to operate in a fine conversion ADC phase. The ADC module 110 may then control the multiplexed sequence 104 to be provided to the first circuitry portion for initial coarse conversion of the analog signal in a sub-sequence and thereafter to the second circuitry portion for fine conversion of the analog signal using an initial approximation from the coarse conversion.

The ADC module 110 illustrated in FIG. 2 will now be further described in relation to operating the ADC module 110 in the coarse conversion ADC phase and the fine conversion ADC phase, respectively. The ADC module 110 may be controlled to selectively activate the coarse conversion ADC phase at initiation of a sub-sequence within the multiplexed sequence 104, as illustrated by control signals coarse/fine in FIG. 2.

The ADC module 110 comprises an input 112, which determines an input signal as a difference of the multiplexed sequence 104 and a feedback signal from the coarse conversion ADC phase. The ADC module 110 further comprises a first demultiplexer 114 and a first multiplexer 116 for selectively operating in the coarse conversion ADC phase or the fine conversion ADC phase. When a signal to select the coarse conversion ADC phase is received in the first demultiplexer 114 and the first multiplexer 116, the input signal passes through the first demultiplexer 114 and the first multiplexer 116 without being further processed.

The ADC module 110 further comprises a quantizer 118, which receives the input signal. The quantizer 118 may be a single-bit quantizer 118, which is used by the coarse conversion ADC phase for determining a value of a single bit in a digital value representing the analog signal. The quantizer 118 may thus output a quantized signal corresponding to a logical zero or a logical one.

The ADC module 110 further comprises a second demultiplexer 120 for selectively operating in the coarse conversion ADC phase or the fine conversion ADC phase. When a signal to select the coarse conversion ADC phase is received in the second demultiplexer 120, the quantized signal is provided to a successive approximation register (SAR) logic 122. The SAR logic 122 may set a digital output based on the received quantized signal. The digital output may further be provided to a second multiplexer 123, which when selected to operate in the coarse conversion ADC phase receives the digital output and passes the digital output to a multi-bit digital-to-analog converter (DAC) 124.

The multi-bit DAC 124 may form an analog feedback signal of the digital output form the SAR logic 122 and provide the analog feedback signal as feedback to the input 112.

In operation, the coarse conversion ADC phase uses successive approximation to quickly determine a coarse digital value representing the analog signal.

The SAR logic 122 may be initialized by setting a most significant bit of a coarse digital output to 1 (while all remaining bits are set to zero). The multi-bit DAC 124 then forms an analog feedback signal which may be compared to the analog signal of the multiplexed sequence 104. Based on the comparison, as determined by the quantizer 118, the SAR logic 122 may determine whether the most significant bit is to be set to zero or one. Then, using the determined bit value of the most significant bit, the SAR logic 122 may proceed to a second most significant bit, setting it to 1 (while all remaining less significant bits are set to zero) and providing a coarse digital output to the multi-bit DAC 124.

The coarse conversion ADC phase may proceed iteratively to determine a bit value with every cycle of the coarse conversion ADC phase. Hence, a successive approximation analog-to-digital conversion may quickly provide a coarse digital value of the analog signal. In one embodiment, the coarse conversion ADC phase may require only B cycles, where B indicates the number of bits of the DAC.

A purpose of the coarse conversion ADC phase is to quickly settle the feedback to the new offset value (and without saturating a modulator of the ADC circuitry 100). At an end of the coarse conversion phase, a coarse digital value is provided as an initial approximation to the fine conversion ADC phase.

At the end of the coarse conversion phase, the ADC module 110 may be controlled to selectively activate the fine conversion ADC phase, as illustrated by control signals coarse/fine in FIG. 2.

As mentioned above, the fine conversion ADC phase may receive an initial approximation of the analog signal from the coarse conversion ADC phase. The initial approximation may be received in a digital integrator 130 of the fine conversion ADC phase. The digital integrator 130 may provide a digital output to the second multiplexer 123, which when selected to operate in the fine conversion ADC phase receives the digital output from the digital integrator 130 and passes the digital output to the multi-bit DAC 124.

The digital integrator 130 and the multi-bit DAC 124 are configured to provide a delta modulation feedback signal to the input 112 for enabling tracking of the analog signal.

At the input 112, an input signal is determined as a difference of the multiplexed sequence 104 and the delta modulation feedback signal from the fine conversion ADC phase. The input signal is provided to the first demultiplexer 114, which when selected to operate in the fine conversion ADC phase, passes the input signal to an inner delta-sigma modulator 132 of the fine conversion ADC phase. The inner delta-sigma modulator 132 determines a difference at an input 134 between the input signal and an inner feedback and provides the difference to an inner integrator 136 that outputs an integrated difference signal. The integrated difference signal is provided to the first multiplexer 116, which when selected to operate in the fine conversion phase takes input from the inner integrator 136 and passes it to the quantizer 118.

The quantizer 118 may generate a digital output in dependence of a level of the integrated difference signal. The digital output is provided to the second demultiplexer 120. When the second demultiplexer 120 is selected to operate in the fine conversion ADC phase, the digital output is passed to an inner DAC 138 of the inner delta-sigma modulator 132, which converts the digital output to an analog inner delta feedback provided at the input 134.

The inner delta-sigma modulator 132 may be configured as a continuous-time delta-sigma modulator 132. The inner delta-sigma modulator 132 may further be configured as an incremental ADC, whereby the inner integrator 136 is reset before the fine conversion ADC phase is performed. The resetting of the inner integrator 136 may be performed when the fine conversion ADC phase is initiated. However, since the inner integrator 136 is not used during the coarse conversion ADC phase, the resetting of the inner integrator 136 may e.g. be performed during the coarse conversion ADC phase. During the fine conversion ADC phase, the estimation of the multiplexed sequence 104 is determined.

The fine conversion ADC phase may track the analog signal regardless of a value of the initial approximation from the coarse conversion phase so that the coarse conversion ADC phase does not set limits on a range of possible digital values that may later be determined by the fine conversion ADC phase. In particular, the fine conversion ADC phase does not digitize a residue of the coarse conversion ADC phase.

The second demultiplexer 120 is also configured to pass the digital output from the inner quantizer 118 to the digital integrator 130 such that the digital integrator 130 and the multi-bit DAC 124 are configured to provide the delta modulation feedback signal to the input 112 for enabling tracking of the analog signal and the fine conversion ADC phase forms a delta-delta-sigma modulator ADC.

After receiving the coarse digital value from the coarse conversion ADC phase, the fine conversion ADC phase operates completely separately from the coarse conversion ADC phase. Thus, the tracking of the analog signal is not constrained by the coarse digital value determined by the coarse conversion ADC phase and the analog signal may be tracked even if assuming values outside a range as may be defined by the coarse digital value.

As evident from the above discussion, the fine conversion ADC phase and the coarse conversion ADC phase may share one or more components. For instance, the fine conversion ADC phase and the coarse conversion ADC phase may share the quantizer 118 and/or the multi-bit DAC 124.

The fine conversion ADC phase may be configured to provide the digital output from the digital integrator 130 to a decimation filter 140. The decimation filter 140 may provide down-sampling to provide an average of oversampled data from the fine conversion ADC phase, providing a higher resolution value of the analog signal at a lower rate. The decimation filter 140 may down-sample the output from the fine conversion ADC phase to the Nyquist rate.

The ADC module 110 may further comprise an element selection logic for dynamic-element-matching. The element selection logic may be used in the fine conversion ADC phase for dynamic-element-matching (DEM) of the multi-bit DAC 124. The non-linearity of the DAC 124 in fine conversion ADC phase may thus be reduced using a mismatch-shaping algorithm. According to an embodiment, Dynamic Weighted Averaging (DWA) may be applied during the fine conversion ADC phase. DEM may not be possible to use in the coarse conversion ADC phase, since the coarse conversion ADC phase may not provide oversampling of data. This may also imply that initial oversampled values provided by the digital integrator 130 may have larger errors caused by the non-linearity of the coarse conversion ADC phase.

The decimation filter 140 may be set to use weights of the oversampled values, wherein different weights may be provided to different oversampled values. The use of different weights to different oversampled values may reduce the effects of non-linearity of the multi-bit DAC 124 that is used in the coarse conversion ADC phase. Thus, by giving a higher weight to last oversampled values in the fine conversion ADC phase compared to initial oversampled values, a contribution of the initial oversampled values is reduced and an error in initial values caused by the non-linearity of the coarse conversion ADC phase may be diminished or reduced.

It should be realized that the inner delta-sigma modulator 132 could also in some embodiments use a DAC 138, as illustrated in FIG. 2. In such case, DEM may also be used in the inner delta-sigma modulator 132, in case a multi-bit quantizer is employed.

As discussed above, the coarse conversion ADC phase may be used for quickly settle the feedback to the new offset value of a sub-sequence within the multiplexed sequence 104. Thereafter, the fine conversion ADC phase may be used for tracking the analog signal during the sub-sequence. At the end of the sub-sequence, a value of the analog signal may be stored in a memory and the ADC circuitry 100 may thus comprise one memory capacity to store one value per analog signal included in the multiplexed sequence 104. The stored value may then be used in a subsequent sub-sequence for the analog signal (from the same sensor) within the multiplexed signal 104. Thus, at initiation of the subsequent sub-sequence, the stored value may be provided as an initial approximation to the coarse conversion ADC phase such that successive approximation may start from the stored value and may even more quickly determine a coarse digital value.

The stored value may alternatively be used in an initial comparison to determine whether a coarse conversion ADC phase is necessary at initiation of the subsequent sub-sequence. For instance, if it is determined in the initial comparison that a difference between the analog signal of the subsequent sub-sequence and the stored value is below a threshold, the ADC module 110 may immediately proceed to operate in the fine conversion ADC phase.

Figure 3:
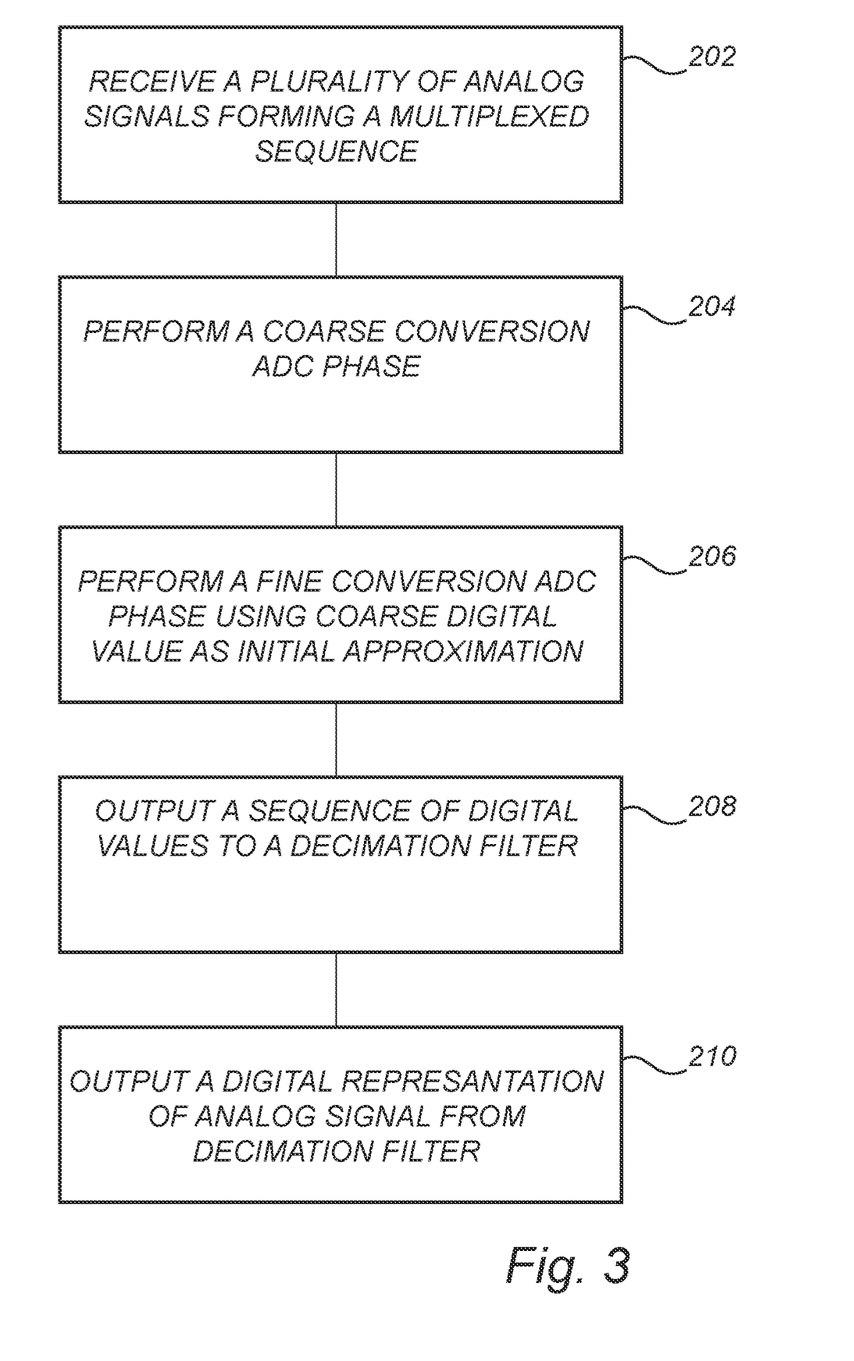
FIG. 3 is a flowchart of a method according to an embodiment.

Referring now to FIG. 3, a method for analog-to-digital conversion will be briefly discussed. The method may be performed by the ADC circuitry 100 described above.

Although the method is described in relation to a multiplexed sequence, it should be realized that the analog-to-digital conversion may alternatively be applied to a single analog signal.

The method may comprise receiving 202 a plurality of analog signals forming a time division multiplexed sequence 104.

The method may further comprise performing 204 a coarse conversion ADC phase at initiation of a sub-sequence of an analog signal within the sequence of the plurality of analog signals. The coarse conversion ADC phase may use successive approximation for determining a coarse digital value of the analog signal of the sub-sequence. The successive approximation may start at an initial value based on an end value of the analog signal of a previous sub-sequence. In the first sub-sequence of the analog signal, the successive approximation may start at an initial default value, such as initiating the default value to zero.

The method may further comprise performing 206 a fine conversion ADC phase using the coarse digital value as an initial approximation of the analog signal, wherein the fine analog-to-digital conversion uses a delta modulation loop for tracking the analog signal during the sub-sequence.

Thanks to the coarse conversion ADC phase, the analog-to-digital conversion may quickly settle. Then, the fine conversion ADC phase may use the coarse digital value as an initial approximation in tracking the analog signal.

The method may further comprise outputting 208 a sequence of analog-to-digital converted values from the fine analog-to-digital conversion to a decimation filter, and outputting 210 a digital representation of the sub-sequence of the analog signal from the decimation filter.

Figure 4:
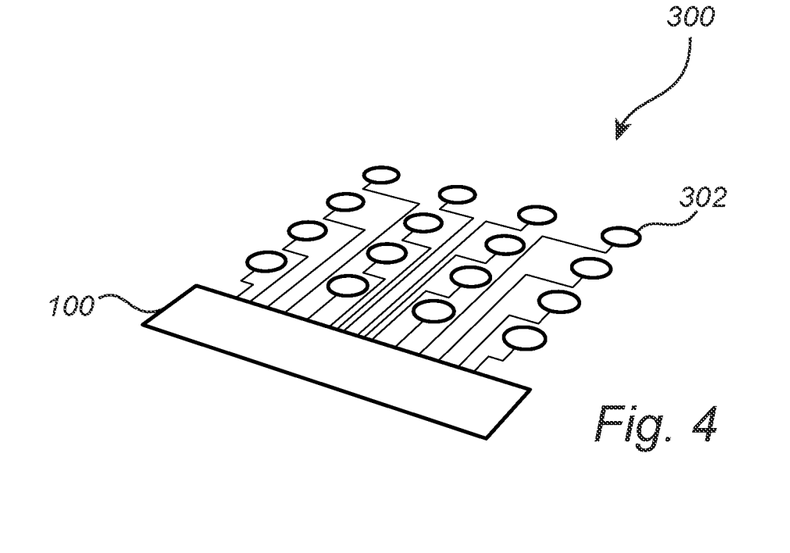
FIG. 4 is a schematic view of a sensor unit according to an embodiment.

Referring now to FIG. 4, the ADC circuitry 100 may be used in a sensor unit 300. The sensor unit 300 may comprise a set of sensors 302.

The set of sensors 302 may for instance comprise an array of sensors 302, which may be configured to each detect a property, such that a spatial distribution of the property may be determined by means of the array of sensors 302.

As the ADC circuitry 100 is compact and may support a plurality of sensors 302, the ADC circuitry 100 may be arranged below the array of sensors 302. This implies that the sensor unit 300 may be very compact and may occupy a small area.

It should be realized that the types of sensors 302 may vary in dependence of the property to be detected.

The sensors 302 may be configured to directly detect an electrical signal, wherein the sensors 302 may e.g. be provided in the form of electrodes. Alternatively, the sensors 302 may be configured to generate an electrical signal representing the detected property.

The sensor unit 300 is particularly useful in applications where the set of sensors 302 may have significant DC offset variations, as the coarse conversion ADC phase allows the ADC circuitry 100 to quickly settle on a new analog signal value which may significantly differ from a previous analog signal value in the multiplexed sequence 104.

The sensor unit 300 may comprise a plurality of ADC circuitries 100, wherein each ADC circuitry 100 is configured to perform analog-to-digital conversion for signals from a unique subset of the set of sensors 302. For instance, the set of sensors 302 may be divided into subsets in a range of 4-64 sensors 302. Each subset may be associated with a separate ADC circuitry 100, which is configured to receive the analog signals from the subset of sensors 302 and to provide analog-to-digital conversion of these analog signals.

Figure 5:
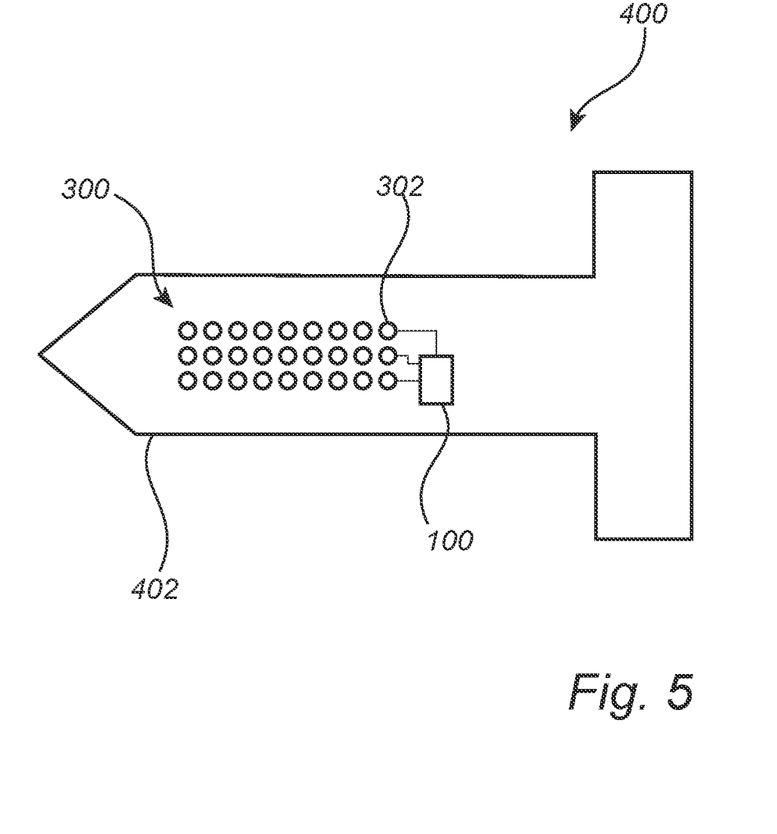
FIG. 5 is a schematic view of a neural probe according to an embodiment.

Referring now to FIG. 5, the use of the sensor unit 300 in a neural probe 400 is illustrated.

The neural probe 400 may comprise a large number of electrodes 302, which are being used to collect neural signals invasively from within neural tissue. To reduce damage of the insertion of the neural probe 400, the probe 400 should have a small cross-sectional area. The neural probe 400 may comprise a carrier 402 for carrying the set of electrodes 302, which carrier 402 is adapted for insertion into neural tissue, e.g. comprising a pointed tip. Therefore, it is beneficial to share wires for transmitting signals from the electrodes 302 to circuitry arranged external to neural tissue.

The ADC circuitry 100 described above is therefore well suited for use with a neural probe 400. As the ADC circuitry 100 is compact, it may be arranged in the portion of the neural probe 400 being inserted into neural tissue. However, since the ADC circuitry 100 also supports multiplexing of analog signals being provided to an ADC module 110, the ADC module 110 or part of it may be arranged external to neural tissue while allowing few wires to be used in the neural probe 400 for transmitting the analog signals to the ADC module 110. It may however be advantageous to arrange the ADC circuitry 100 with the ADC module 110 in the portion of the neural probe 400 being inserted into neural tissue, since it may avoid external interferences affecting the signals being transmitted in wires of the neural probe 400.

Further, the DC offset of electrodes 302 in a neural probe 400 may typically vary significantly between different electrodes 302 due to large and random DC offsets caused by the electrode-brain interface. Therefore, the ADC circuitry 100, which is configured to handle large variations in DC offset in a time-multiplexed sequence 104, is particularly useful with the neural probe 300. The ADC circuitry 100 allows quickly settling to a new DC offset level at initiation of a sub-sequence in the multiplexed sequence 104 and thereafter tracking the analog signal using the fine conversion ADC phase.

Figure 6:
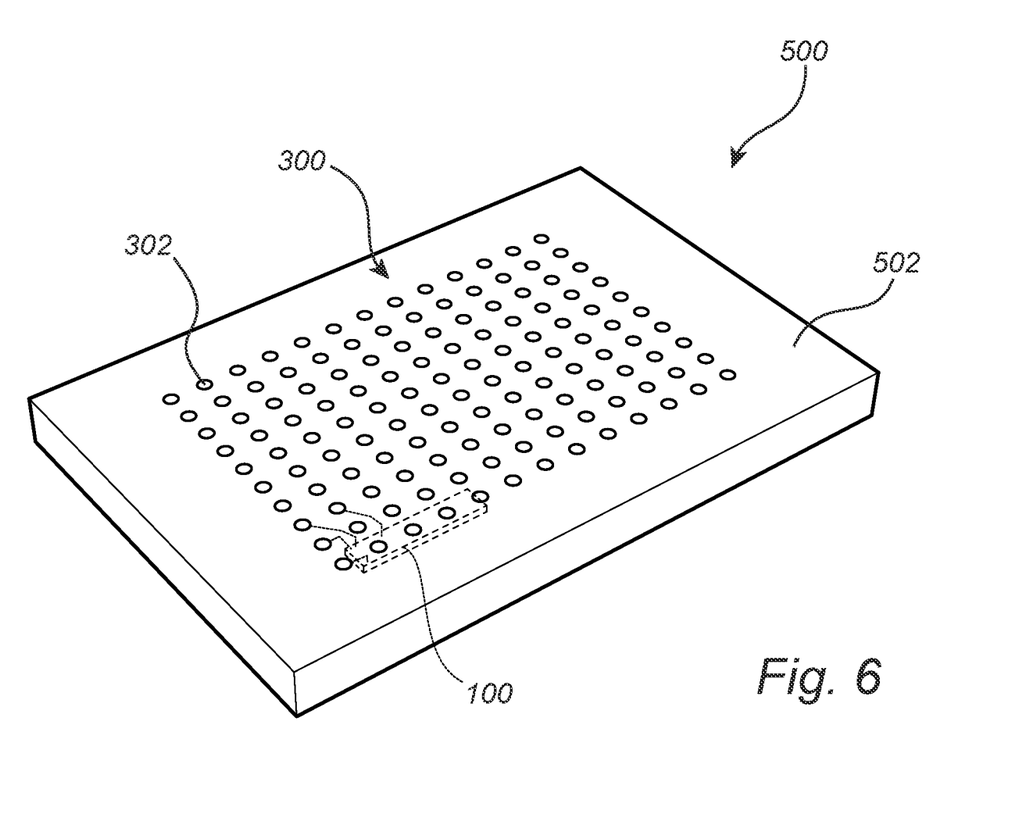
FIG. 6 is a schematic view of a micro-electrode array according to an embodiment.

Referring now to FIG. 6, the use of the sensor unit 300 in a micro-electrode array 500 is illustrated.

The micro-electrode array 500 may comprise a large number of electrodes 302. Thanks to the use of the ADC circuitry 100 that may support a plurality of electrodes 302, while enabling handling of large variations in DC offset, an area of circuitry needed for analog-to-digital conversion of recorded signals may be reduced.

The micro-electrode array 500 may comprise a carrier 502 for carrying the set of electrodes 302. The carrier 502 may comprise a surface for receiving a sample of biological matter. For instance, the carrier 502 may be configured to allow growth of cells on the micro-electrode array 500 such that electrical signals of the cells may then be studied by the micro-electrode array 500.

Further, the ADC circuitry 100 may be arranged below the set of electrodes 302 on the carrier 502 of the micro-electrode array 500. Thereby the need of routing analog signals to a periphery of the micro-electrode array 500 may be avoided. This can also enable the integration of a larger number or a higher density of electrodes 302, or a larger number of electrodes 302 that can be simultaneously recorded, since the number of wires required for each subset of the electrodes 302 can be reduced.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, the inner delta-sigma modulator 132 discussed above and illustrated in FIG. 2 is a first order modulator. However, it should be realized that a delta-sigma modulator of higher order may be used instead.

The invention claimed is:

1. An analog-to-digital converter, ADC, module,
   wherein the ADC module is configured to operate in a coarse conversion ADC phase, and a fine conversion ADC phase comprising a delta modulation loop for tracking a signal,
   wherein the ADC module is configured to, at initiation of input of an analog signal, operate in the coarse conversion ADC phase for determining a coarse digital value of the analog signal;
   wherein the ADC module is configured to, when the coarse digital value is determined, operate in the fine conversion ADC phase, wherein the ADC module operating in the fine conversion ADC phase is configured to receive the coarse digital value as an initial approximation of the analog signal in an integrator of the delta modulation loop and is configured to track the analog signal during a finite duration.

2. The ADC module according to claim 1, wherein the ADC module in the fine conversion ADC phase provides an incremental ADC.

3. The ADC module according to claim 2, wherein the ADC module in the fine conversion ADC phase provides a delta-delta-sigma modulator ADC comprising an inner delta-sigma modulator with an outer delta modulator.

4. The ADC module according to claim 3, wherein the outer delta modulator comprises a digital integrator followed by a digital-to-analog converter.

5. The ADC module according to claim 1, wherein the ADC module is configured to operate in the coarse conversion ADC phase using successive approximation.

6. The ADC module according to claim 1, wherein the ADC module is connected to a decimation filter for providing output from the ADC module operating in the fine conversion ADC phase to the decimation filter for downsampling of output from the fine conversion ADC phase.

7. The ADC module according to claim 1, wherein the ADC module is configured to be controlled to selectively activate the coarse conversion ADC phase or the fine conversion ADC phase.

8. The ADC module according to claim 7, wherein the ADC module is configured to re-use at least one component, such as a multi-bit DAC and/or a single-bit comparator, when operating in the coarse conversion ADC phase and the fine conversion ADC phase.

9. An ADC circuitry, comprising:
   a multiplexer input configured to receive a plurality of analog signals and configured to output a time division multiplexed sequence of the plurality of analog signals, wherein each of the plurality of analog signals forms at least one sub-sequence within the sequence, and the ADC module according to claim 1;
   wherein the ADC module is configured to, at initiation of a sub-sequence of an analog signal within the sequence of the plurality of analog signals, operate in the coarse conversion ADC phase, and
   wherein the ADC module operating in the fine conversion ADC phase is configured to track the analog signal during the sub-sequence.

10. The ADC circuitry according to claim 9, wherein each of the plurality of analog signals forms at least a first sub-sequence and a second sub-sequence within the sequence, wherein the ADC circuitry further comprises a memory for storing an end value determined by tracking the analog signal during the first sub-sequence, and wherein the ADC module is configured to, at initiation of the second sub-sequence of the analog signal, operate in the coarse conversion ADC phase receiving output from the multiplexer for determining a coarse digital value of the analog signal and receiving the end value from the memory as an initial approximation for determining the coarse digital value.

11. A sensor unit comprising:
   a set of sensors configured to record electrical signals; and
   the ADC circuitry according to claim 9, wherein the ADC circuitry is connected to at least a subset of the set of sensors for receiving the plurality of analog signals.

12. A neural probe comprising:
   a carrier adapted for being inserted into neural tissue of a brain;
   the sensor unit according to claim 11, wherein the set of sensors is arranged on the carrier for recording electrical signals from sensing in the brain.

13. The neural probe according to claim 12, wherein the ADC circuitry is arranged on the carrier.

14. A micro-electrode array, comprising:
   a carrier providing a surface for receiving a sample of biological matter; and
   the sensor unit according to claim 11, wherein the set of sensors is arranged on the carrier for recording electrical signals in the sample of biological matter.

15. The micro-electrode array according to claim 14, wherein the ADC circuitry is arranged on the carrier.

16. A method for analog-to-digital conversion, said method comprising:
receiving an analog signal;
at initiation of the analog signal, performing a coarse analog-to-digital conversion for determining a coarse digital value of the analog signal;
performing a fine analog-to-digital conversion using the coarse digital value as an initial approximation of the analog signal, wherein the fine analog-to-digital conversion uses a delta modulation loop for tracking the analog signal during a finite duration.

\* \* \* \* \*